United States Patent
Lamph et al.

(10) Patent No.: US 7,259,188 B2
(45) Date of Patent: Aug. 21, 2007

(54) METHODS AND PHARMACEUTICAL COMPOSITIONS FOR TREATMENT OF ANTI-ESTROGEN RESISTANT BREAST CANCER USING RXR MODULATORS

(75) Inventors: William W. Lamph, La Jolla, CA (US); Eric D. Bischoff, Encinitas, CA (US); Richard A. Heyman, Encinitas, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 487 days.

(21) Appl. No.: 10/229,649

(22) Filed: Aug. 27, 2002

(65) Prior Publication Data

US 2003/0013766 A1   Jan. 16, 2003

Related U.S. Application Data

(63) Continuation of application No. 09/327,117, filed on Jun. 7, 1999, now abandoned.

(60) Provisional application No. 60/089,104, filed on Jun. 12, 1998.

(51) Int. Cl.
*A61K 31/135* (2006.01)
*A61K 31/07* (2006.01)

(52) U.S. Cl. .................. 514/651; 514/648; 514/725

(58) Field of Classification Search ............. 514/648, 514/569
See application file for complete search history.

(56) References Cited

U.S. PATENT DOCUMENTS

| | | |
|---|---|---|
| 4,193,931 A | 3/1980 | Loeliger |
| 4,326,055 A | 4/1982 | Loeliger |
| 4,539,134 A | 9/1985 | Martin et al. |
| 4,578,498 A | 3/1986 | Frickel et al. |
| 4,801,733 A | 1/1989 | Wuest et al. |
| 4,831,052 A | 5/1989 | Shudo |
| 4,833,240 A | 5/1989 | Maignan et al. |
| 4,874,747 A | 10/1989 | Shroot et al. |
| 4,877,805 A | 10/1989 | Kligman |
| 4,879,284 A | 11/1989 | Lang et al. |
| 4,888,342 A | 12/1989 | Kligman |
| 4,889,847 A | 12/1989 | Kligman et al. |
| 4,898,864 A | 2/1990 | Maignan et al. |
| 4,925,979 A | 5/1990 | Shudo |

(Continued)

FOREIGN PATENT DOCUMENTS

CA   2034220   1/1991

(Continued)

OTHER PUBLICATIONS

Pfahl, retinoid related molecules: new promises against lung and breast cancer, Exp. Opin. Invest. Drugs (Apr. 1998), 7(4), pp. 601-606.*

(Continued)

*Primary Examiner*—Phyllis G. Spivack
*Assistant Examiner*—James D. Anderson
(74) *Attorney, Agent, or Firm*—Fish & Richardson P.C.; Stephanie Seidman; Frank J. Miskiel

(57) ABSTRACT

Methods and compositions for the treatment of anti-estrogen resistant breast cancer using retinoid compounds which are modulators of Retinoid X Receptors.

18 Claims, 2 Drawing Sheets

U.S. PATENT DOCUMENTS

| | | | |
|---|---|---|---|
| 4,981,784 A | 1/1991 | Evans et al. | |
| RE33,533 E | 2/1991 | Shroot et al. | |
| 5,004,730 A | 4/1991 | Philippe et al. | |
| 5,071,773 A | 12/1991 | Evans et al. | |
| 5,124,473 A | 6/1992 | Shroot et al. | |
| 5,198,567 A | 3/1993 | Lang et al. | |
| 5,298,429 A | 3/1994 | Evans et al. | |
| 5,391,569 A | 2/1995 | Brion et al. | |
| 5,399,586 A | 3/1995 | Davies et al. | |
| 5,409,930 A | 4/1995 | Spada et al. | |
| 5,455,265 A | 10/1995 | Chandraratna | |
| 5,466,861 A | 11/1995 | Dawson et al. | |
| 5,506,102 A | 4/1996 | McDonnell | |
| 5,508,456 A | 4/1996 | Boehm | 554/163 |
| 5,514,821 A | 5/1996 | Bennani et al. | 554/221 |
| 5,552,271 A | 9/1996 | Pfahl et al. | |
| 5,585,244 A | 12/1996 | Allegretto et al. | 435/7.1 |
| 5,656,643 A | 8/1997 | Spada et al. | |
| 5,710,158 A | 1/1998 | Myers et al. | |
| 5,721,103 A | 2/1998 | Boehm et al. | 435/7.1 |
| 5,770,378 A | 6/1998 | Hwang et al. | 435/7.1 |
| 5,770,382 A | 6/1998 | Hwang et al. | 435/7.1 |
| 5,770,383 A | 6/1998 | Hwang et al. | 435/7.1 |
| 5,780,676 A * | 7/1998 | Boehm et al. | 562/490 |
| 5,801,253 A | 9/1998 | Klaus et al. | |
| 5,817,845 A | 10/1998 | White et al. | 554/154 |
| 5,824,484 A | 10/1998 | Pfahl et al. | |
| 5,837,725 A | 11/1998 | Dawson et al. | |
| 5,932,622 A | 8/1999 | Evans et al. | 514/725 |
| 5,962,731 A | 10/1999 | Boehm et al. | 562/460 |
| 5,968,989 A | 10/1999 | Evans et al. | 514/725 |
| 5,972,881 A | 10/1999 | Heyman et al. | 514/3 |
| 5,998,654 A | 12/1999 | Boehm et al. | 560/45 |
| 6,028,052 A | 2/2000 | Heyman et al. | 514/3 |
| 6,043,279 A | 3/2000 | Boehm et al. | 514/568 |
| 6,083,977 A | 7/2000 | Boehm et al. | 514/457 |
| 6,218,430 B1 | 4/2001 | Allegretto et al. | 514/475 |
| 6,228,862 B1 | 5/2001 | Heyman et al. | 514/277 |
| 6,316,404 B1 | 11/2001 | Heyman et al. | 514/3 |
| 6,320,074 B1 | 11/2001 | Boehm et al. | 562/490 |
| 6,521,633 B2 | 2/2003 | Heyman et al. | 514/277 |
| 6,545,049 B1 | 4/2003 | Canan-Koch et al. | 514/569 |
| 6,576,676 B1 | 6/2003 | Evans et al. | 514/725 |
| 6,593,493 B1 | 7/2003 | Ardecky et al. | 562/465 |
| 6,610,883 B1 | 8/2003 | Boehm et al. | 562/490 |

FOREIGN PATENT DOCUMENTS

| | | |
|---|---|---|
| EP | 0 718 285 B1 | 6/1996 |
| WO | WO89/05355 A1 | 6/1989 |
| WO | WO91/06677 A1 | 5/1991 |
| WO | WO92/05477 A1 | 4/1992 |
| WO | WO92/20642 A1 | 11/1992 |
| WO | WO93/03944 A1 | 3/1993 |
| WO | WO93/10094 A1 | 5/1993 |
| WO | WO93/11235 A1 | 6/1993 |
| WO | WO93/11755 A1 | 6/1993 |
| WO | WO93/21146 A1 | 10/1993 |
| WO | WO93/23431 A1 | 11/1993 |
| WO | WO94/15902 A1 | 7/1994 |
| WO | WO94/20093 A1 | 9/1994 |
| WO | WO94/23068 A1 | 10/1994 |
| WO | WO95/04036 A1 | 2/1995 |
| WO | WO95/15758 A1 | 6/1995 |
| WO | WO95/18380 A1 | 7/1995 |
| WO | WO96/05165 A1 | 2/1996 |
| WO | WO96/19458 A1 | 6/1996 |
| WO | WO96/20913 A1 | 7/1996 |
| WO | WO97/12853 A1 | 4/1997 |
| WO | 99/08682 | 2/1999 |

OTHER PUBLICATIONS

Fitzgerald et al., Cancer Research, vol. 57, No. 13, (Jul. 1, 1997), pp. 2642-2650.*

Allegretto, E., et al., "Retinoid X Receptor Acts as a Hormone Receptor In Vivo to Induce a Key Metabolic Enzyme for 1,25-Dihydroxyvitamin $D_3$," *J. Bio. Chem.*, 270(41):23906-23909 (1995).

Antras, et al., "Adipsin Gene Expression in 3T3-F442A Adipocytes Is Posttranscriptionally Down-Regulated by Retinoic Acid," *J. Bio. Chem.*, 266(2):1157-1161 (1991).

Beard, et al., "Synthesis and Structure-Activity Relationships of Stilbene Analogs Substituted with Heteromatic Carboxylic Acids," *J. Med. Chem.*, 38:2820-2829 (1995).

Bischoff, et al., *Cancer Research*, 58(3):479-484 (1998).

Bissonnette, R., et al., "9-*cis* Retinoic Acid Inhibition of Activation-Induced Apoptosis Is Mediated via Regulation of Fas Ligand and Requires Retinoic Acid Receptor and Retinoid X Receptor Activation," *Mollecular and Cellular Biology*, 15(10):5576-5585 (1995).

Boehm, M., et al., *J. Med. Chem.*, 37:2930 (994).

Boehm, M., et al., "Design and Synthesis of Potent Retinoid X Receptor Selective Ligands That Induce Apoptosis in Leukemia Cells," *J. Med. Chem.*, 38(16):3146-3155 (1995).

Canan Koch, S. et al., "Identification of the First Retinoid X Receptor Homodimer Antagonist," *J. Med. Chem.*, 39(17):3229-3234 (1996).

Dawson, M., et al., "Effect of Structural Modifications in the C7-C11 Region of the Retinoid Skeleton on Biological Activity in a Series of Aromatic Retinoids," *J. Med. Chem.*, 32:1504-1517 (1989).

Dawson, M., et al., *Chemistry and Biology of Synthetic Retinoids*, Chapters 3, 8, 14, and 16, CRC Press, Inc., Florida (1990).

Dawson, M., et al., "The Synthetic Chemistry of Retinoids," *The Retiniods: Biology, Chemistry and Medicine*, Raven Press, pp. 5-178 (1994).

Evans, et al., "The Steroid and Thyroid Hormone Receptor Superfamily," *Science*, 240:889-895 (1988).

Fingl, E., et al., "General Principles," *The Pharmacological Basis of Therapeutics*, pp. 1-46 (1975).

Fitzgerald, et al., *Cancer Research*, 57(13):2642-2650 (1997).

Gennaro, Alfonso, R., et al., *Remmington's Pharmaceutical Sciences*, 18th Edition, Mack Publishing Co., Easton PA (1990).

Giguere, V., et al., "Identification of a Receptor for the Morphogen Retinoic Acid," *Nature*, 330(17):624-629 (1987).

Gottardis, M., et al., "Chemoprevention of Mammary Carcinoma by LGD1069 (Targretin): An RXR-Selective Ligand," *Cancer Research*, 56:5566-5570 (1996).

Heyman, R., et al., "9-Cis Retinoic Acid is a High Affinity Ligand for the Retinoid X Receptor," *Cell*, 68:397-406 (1992).

Kagechika, H., et al., "Retinobenzoic Acids. 2. Structure-Activity Relationships of Chalcone-4-Carboxylic Acids and Flavone-4'-Carboxylic Acids," *J. Med. Chem.*, 32:834-840 (1989).

Kagechika, H., et al., "Retinobenzoic Acids. 3. Structure-Activity Relationships of Retinoidal Azobenzene-4-Carboxylic Acids and Stilbene-4-Carboxylic Acids," *J. Med. Chem.*, 32:1098-1108 (1989).

Kagechika, H., et al., "Retinobenzoic Acids. 4. Conformation of Aromatic Amides with Retinoidal Activity. Importance of *trans*-Amide Structure for the Activity," *J. Med. Chem.*, 32:2292-2296 (1989).

Levin, A., et al., "9-*Cis* Retinoic Acid Stereoisomer Binds and Activated the Nuclear Receptor RXRα," *Nature*, 355:359-361 (1992).

Liu, R., et al., "Photochemistry and Synthesis of Stereoisomers of Vitamin A," *Tetrahedron Letters*, 40(11):1931-1969 (1984).

Loeliger, P., et al., "Arotinoids, A New Class of Highly Active Retinoids," *Eur. J. Med. Chem.*, 1:9-15 (1980).

Mangelsdorf, D., et al., "A Direct Repeat in the Cellular Retinol-Binding Protein Type II Gene Confers Differential Regulation by RXR and PAR," *Cell*, 66:555-561 (1991).

Mangelsdorf, D., et al., "The Retinoid Receptors," *The Retiniods: Biology, Chemistry and Medicine*, Raven Press, pp. 319-349 (1994).

Miller, et al., *J. Clinical Oncology*, 15(2)790-795 (1997).

Petkovich, M., et al., "A Human Retinoic Acid Receptor Which Belongs to the Family of Nuclear Receptors," *Nature*, 330:444-450 (1987).

Pfahl, M., "Retinoid Related Molecules: New Promises Against Lung and Breast Cancer," *Exp. Opin. Invest. Drugs*, 7(4):601-606 (1998).

Safonova, I., et al., "Retinoids are positive effectors of adipose cell differentiation," *Mollecular and Cellular Endocrinology*, 104:201-211 (1994).

Salazar-Olivio, F., et al., "Inhibition of 3T3 Adipogenesis by Retinoic Acid is Not Mediated by Cytoplasmic Retinoic Acid-Binding Protein," *Biochem. and Biophys. Res. Comm.*, 204(1):257-263 (1994).

Strickland, S., et al., "Structure-Activity Relationships of a New Series of Retinoidal Benzoic Acid Derivatives as Measured by Induction of Differentiation of Murine F9 Teratocarcinoma Cells and Human HL-60 Promyelocytic Leukemia Cells," *Cancer Res.*, 43:5268-5272 (1983).

Zhimin, S., et al., "Retinoic Acid Nuclear Receptor α(RARα) Plays A Major Role in Retinoid-Mediated Inhibition of Growth in Human Breast Carcinoma Cells," *Chinese Med. Sci. J.*, 11(3): 142-146 (1996).

Aboulafia et al., "Retinoid-induced hypercalcemia in a patient with kaposi sarcoma associated with acquired immunodeficiency syndrome," American Journal of Clinical Oncology-Cancer Clinical Trials 21(5): 513-517 (1998).

Aboulafia et al. "V. 9-cis-Retinoic Acid Capsules in the Treatment of AIDS-Related Kaposi Sarcoma: Results of a Phase 2 Multicenter Clinical Trial," Archives of Dermatology 139(2): 178-186 (2003).

Agarwal et al., "Induction of adipocyte-specific gene expression is correlated with mammarytumor regression by the retinoid X receptor-ligand LGD1069 (Targretin)," Cancer Res. 60(21):6033-8 (2000).

Allegretto, E.A. and R.A. Heyman, "Expression and characterization of retinoid receptors in yeast," Methods Enzymol. 282: 25-32 (1997).

Allegretto et al., "Transactivation properties of retinoic acid and retinoid X receptors in Mammalian cells and yeast. Correlation with hormone binding and effects of metabolism," J Biol Chem. 268(35): 26625-33 (1993).

Allegretto et al. "Transactivation properties if retinoic acid and retinoid X receptors in mammalian cells and yeast. Correlation with hormone binding and effects of metabolism," J Biol Chem 269(10):7834 (erratum) (1994).

Allegretto et al., "Retinoid X receptor acts as a hormone receptor in vivo to induce a key metabolic enzyme for 1,25-dihydroxyvitamin D(3)," Journal of Biological Chemistry 271(11): 6562 (erratum) (1996).

Anzano et al., "Prevention of Breast Cancer in the Rat with 9-*cis*-Retinoic Acid as a Single Agent and in Combination with Tamoxifen," Cancer Research 54(17): 4614-4617 (1994).

Bennani et al. "Synthesis and Characterization of a Highly Potent and Selective Isotopically Labeled Retinoic Acid Receptor Ligand, ALRT1550," J Org Chem. 63(3)543-550 (1998).

Bischoff et al., "#2054 Tamoxifen resistance: The RXR-selective ligand LGD1069 causes complete regression of tamoxifen resistant mammary carcinoma," Proceedings of the 90th Annual Meeting of the American Association for Cancer Research, Apr. 10-14, 1999, Philadelphia, PA, 40: 309 (Mar. 1999).

Bischoff et al., "Chemoprevention of mammary carcinoma by Targretin™ (LGD1069): An RXR selective ligand," Breast Cancer Research and Treatment, 41(3): 200 (1996).

Bischoff et al., "Effect of the Retinoid X Receptor-Selective Ligand LGD1069 on Mammary Carcinoma After Tamoxifen Failure," Journal of National Cancer Institute 91(24): 2118-2123 (1999).

Blumberg et al., "Novel retinoic acid receptor ligands in xenopus embryos," Proc. Natl. Sci. U.S.A. 93: 4873-4878 (1996).

Boehm et al., "Synthesis of high specific activity [3H]-9-cis-retinoic acid and itsapplication for identifying retinoids with unusual binding properties," J Med Chem. 37(3)408-14 (1994).

Boehm et al., "A new generation of retinoid drugs for the treatment of dermatological diseases," Emerging Drugs 2:287-303 (1997).

Canan Koch et al, "Synthesis of retinoid X receptor-specific ligands that are potent inducers ofadipogenesis in 3T3-L1 cells," J Med Chem. 42(4):742-50 (1999).

DeGrendele, H., "Current Data with Bexarotene (Targretin) in Non-Small-Cell Lung Cancer," Clinical Lung Cancer 4(4): 210-212 (2003).

Duvic et al., "Phase 2 and 3 clinical trial of oral bexarotene (targretin capsules) for the treatment of refractory or persistent early-stage cutaneous T- cell lymphoma," Archives of Dermatology 137(5): 581-593 (2001).

Elgort et al., "Estrogen and estrogen receptor antagonists stimulate transcription from thehuman retinoic acid receptor-alpha 1 promoter via a novel sequence," Mol Endocrinol. 10(5): 477-87 (1996).

Farmer et al., "Retinoic acid receptor ligands based on the 6-cyclopropyl-2,4-hexadienoic acid," Bioorg Med Chem Lett. 3(2):261-4 (2003).

Gamage et al., "Efficacy of LGD1069 (Targretin), a retinoid X receptor-selective ligand, for treatment of uterine leiomyoma," J Pharmacol Exp Ther. 295(2):677-81 (2000).

Gottardis et al., "#3058 Inhibition of human breast cancer cells in vitro and in vivo by retinoid receptor-selective ligands," Proceedings of the 86th Annual Meeting of the American Association for Cancer Research, Mar. 18-22, 1995, Toronto, Ontario, Canada, 36: 514 (Mar. 1995).

Gottardis et al. "#3059 Anti-tumor efficacy of retinoids in primary human head and neck squamous cell carcinoma xenografts," Proceedings of the 86th Annual Meeting of the American Association for Cancer Research, Mar. 18-22, 1995, Toronto, Ontario, Canada, 36: 514 (Mar. 1995).

Gottardis et al., "The efficacy of 9-cis retinoic acid in experimental models of cancer," Breast Cancer Res Treat. 38(1)85-96 (1996).

Gottardis et al., "Regulation of retinoblastoma gene expression in hormone- dependent breast cancer," Endocrinology 136:5659-5665 (1995).

Guitart et al., "Low dose bexarotene (Targretin (R)) capsules and phototherapy for early stage cutaneous T-cell lymphoma," Abstract 199 in Journal of Investigative Dermatology 119(1):241 (2002).

Hamann, L.G., "An efficient, stereospecific synthesis of the dimer-selective retinoid Xreceptor modulator (2E,4E,6Z)-7-[5,6,7,8-tetrahydro-5,5,8,8-tetramethyl-2-(n-propyloxy)naphthalen-3-yl]-3-methyl octa-2,4, 6-trienoicacid," J Org Chem. 65(10):3233-5 (2000).

Han et al., "Elevated expression of retinoic acid receptor-alpha (RAR alpha) in estrogen-receptor-positive breast carcinomas as detected by immunohistochemistry," Diagn Mol Pathol 6(1): 42-48 (1997).

Harmon et al., "Activation of mammalian retinoid X receptors by the insect growth regulator methoprene," Proc Natl Acad Sci U S A. 92(13):6157-60 (1995).

Hofmann et al., "Oral 9-cis retinoic acid (Alitretinoin) in the treatment of myelodysplastic syndromes: results from a pilot study," Leukemia 14(9): 1583-1588 (2000).

Howell et al., "Effects of retinoid treatment of rats on hepatic microsomal metabolism andcytochromes P450. Correlation between retinoic acid receptor/retinoid x receptorselectivity and effects on metabolic enzymes," Drug Metab Dispos. 26(3):234-9 (1998).

Johnson et al., "Retinoid X receptor (RXR) agonist-induced activation of dominant-negative RXR-retinoic acid receptor alpha403 heterodimers is developmentally regulated during myeloid differentiation," Mol Cell Biol. 19(5):3372-82 (1999).

Kitareewan et al., "Phytol metabolites are circulating dietary factors that activate the nuclear receptor RXR," Mol Biol Cell. 7(8):1153-66 (1996).

Kliewer et al., "Retinoid X receptor-COUP-TF interactions modulate retinoic acid signaling," Proc Natl Acad Sci U S A. 89(4):1448-52 (1992).

Kurie et al., "Treatment of Former Smokers With 9-cis-Retinoic Acid Reverses Loss of Retinoic Acid Receptor- Expression in the Bronchial Epithelium: Results From a Randomized Placebo-Controlled Trial," Journal of the National Cancer Institute 95(3): 206-214 (2003).

Kurokawa et al., "Regulation of retinoid signalling by receptor polarity and allosteric control of ligand binding," Nature 371(6497):528-31 (1994).

Lamph, W.W., "Cross-coupling of AP-1 and intracellular hormone receptors," Cancer Cells. 3(5)183-5 (1991).

Lee et al., "A chimeric thyroid hormone receptor constitutively bound to DNA requiresretinoid X receptor for hormone-dependent transcriptional activation in yeast," Mol Endocrinol. 8(9)1245-52 (1994).

Lipkin et al., "Constitutive retinoid receptors expressed from adenovirus vectors that specifically activate chromosomal target genes required for differentiation of promyelocytic leukemia and teratocarcinoma cells," J Virol. 70(10):7182-9 (1996).

Liu et al., "The Binding Site of Opsin Based on Analog Studies with Isometric, Fluorinated, Alkylated and Other Modified Retinals" Chapter 3 in Chemistry and Biology of Synthetic Retinoids, Dawson, M.I. And W.H. Okamura (Eds.), Boca Raton, Florida: CRC Press, Inc., pp. 51-75 (1990).

Liu et al., "Mechanism of selective retinoid X receptor agonist-induced hypothyroidism in the rat," Endocrinology 143(8):2880-5 (2002).

Mangelsdorf et al., "Characterization of three RXR genes that mediate the action of 9-cis retinoic acid," Genes Dev. 6(3):329-44 (1992).

Martin et al., "Induction of the fatty acid transport protein 1 and acyl-CoA synthase genes by dimer-selective rexinoids suggests that the peroxisome proliferator-activated receptor-retinoid X receptor heterodimer is their molecular target," J Biol Chem. 275(17):12612-8 (2000).

McDonnell et al., "Analysis of estrogen receptor function in vitro reveals three distinct classes of antiestrogens," Mol Endocrinol. 9(6):659-69 (1995).

Miller et al., "Initial clinical trial of the retinoid receptor pan agonist 9-cis retinoic acid," Clinical Cancer Research 2(3): 471-475 (1996).

Miller et al., "Retinoids and the treatment of non-small cell lung cancer: The Memorial Sloan-Kettering experience in 92 patients," Lung Cancer 18 (Suppl 1): 192 (1997).

Miller et al., "9-cis retinoic acid induces complete remission but does not reverse clinically acquired retinoid resistance in acute promyelocytic leukemia," Blood 85(11): 3021-3027 (1995).

Miller et al., "A phase I-II study of 9-cis retinoic acid and interferon-alpha2b in patients with advanced renal-cell carcinoma: an NCIC Clinical Trials Group study," Annals of Oncology 11(11): 1387-1389 (2000).

Monczak et al., "Induction of apoptosis without differentiation by retinoic acid in PLB-985 cells requires the activation of both RAR and RXR," Blood 90(9): 3345-3355 (1997).

Moon et al., "Effect of retinol in preventing squamous cell skin cancer in moderate-risk subjects: A randomized, double-blind, controlled trial," Cancer Epidemiology Biomarkers & Prevention 6(11): 949-956 (1997).

Mukherjee et al., "Identification, characterization, and tissue distribution of human peroxisomeproliferator-activated receptor (PPAR) isoforms PPARgamma2 versus PPARgammal andactivation with retinoid X receptor agonists and antagonists," J Biol Chem. 272(12):8071-6 (1997).

Nagy et al., "Retinoid-induced apoptosis in normal and neoplastic tissues," Cell Death & Differentiation 5(1): 11-19 (1998).

Nowfar et al., "Tumor prevention by 9-cis-retinoic acid in the N-nitroso-N-methylurea model of mammary carcinogenesis is potentiated by the pineal hormone melatonin," Breast Cancer Res Treat. 72(1):33-43 (2002).

Ortiz et al., "Retinoids in combination therapies for the treatment of cancer: mechanisms and perspectives," Drug Resistance Updates 5(3-4): 162-175 (2002).

Pathirana et al., "Identification of an activator of the retinoid X receptor," J Nat Prod. 57(10):1458-61 (1994).

Peter et al., "Effects of retinoids on human breast cancer cell proliferation and RAR- and RXR-gene expression in vitro," Breast Cancer Research and Treatment 46(1): 110 (1997).

Pettersson et al., "Retinoids cause apoptosis in pancreatic cancer cells via activation of RAR-gamma and altered expression of Bcl-2/Bax," British Journal of Cancer 87(5): 555-561 (2002).

Press Release: Nov. 8, 2000 "Ligand's Targretin May Extend Survival in Lung Cancer Patients; Data Reported at the NCI-EORTC-AACR Meeting," http://www.corporate-ir.net/ireye/ir_site.zhtml?ticker=LGND&script=400 (accessed on Feb. 3, 2005).

Press Release: Dec. 5, 2000 "Ligand's ONTAK in Combination With Steroids Doubled Overall Response Rate In CTCL; Three Posters on ONTAK and Targretin at American Society of Hematology Meeting," http://www.corporate-ir.net/ireye/ir_site.zhtml?ticker=LGND&script=400 (accessed on Feb. 3, 2005).

Press Release: Dec. 9, 2002 Ligand's Targretin Prevents Development of Mammary Tumors in Pre-Clinical Study of ER-Negative Breast Cancer, Journal Article Reports http://www.corporate-ir.net/ireye/ir_site.zhtml?ticker=LGND&script=400 (accessed on Feb. 3, 2005).

Press Release: Feb. 28, 2002 "Targretin Gel Achieved 86% Response Rate in Early-Stage CTCL Patients Treated for More Than One Year, Researchers Report At AAD Meeting," http://www.corporate-ir.net/ireye/ir_site.zhtml?ticker=LGND&script=400 (accessed on Feb. 3, 2005).

Press Release: Mar. 13, 2000 "Targretin Capsules Benefit Patients with All Stages of Cutaneous T-Cell Lymphoma; Results of Phase III Trials Presented at American Academy of Dermatology Meeting," http://www.corporate-ir.net/ireye/ir_site.zhtml?ticker=LGND&script=400 (accessed on Feb. 3, 2005).

Press Release: Mar. 24, 2003 "Four Clinical Trials Presented at AAD Show Ligand's Targretin, Panretin Demonstrate Promising Activity in Range of Dermatologic Disorders," http://www.corporate-ir.net/ireye/ir_site.zhtml?ticker=LGND&script=400 (accessed on Feb. 3, 2005).

Press Release: Mar. 29, 2004 "New Findings Presented at AACR Show Ligand's Targretin Synergizes with Chemotherapeutic Agents to Arrest NSCLC Growth and Prevents or Reverses Acquired Paclitaxel and Taxol Resistance in NSCLC and Advanced Breast Cancer," http://www.corporate-ir.net/ireye/ir_site.zhtml?ticker=LGND&script=400 (accessed on Feb. 3, 2005).

Press Release: Apr. 8, 2003 "Ligand's Targretin Combined With Taxol Prevents and Overcomes Acquired Taxol Resistance in Vitro and in Vivo, Preclinical Breast Cancer Studies Demonstrate," http://www.corporate-ir.net/ireye/ir_site.zhtml?ticker=LGND&script=400 (accessed on Feb. 3, 2005).

Press Release: May 14, 2001 "Targretin Capsules May Improve Survival in Patients with Advanced Renal Cell Cancer; Combination Therapy May Delay Disease Progression," http://www.corporate-ir.net/ireye/ir_site.zhtml?ticker=LGND&script=400 (accessed on Feb. 3, 2005).

Press Release: May 15, 2001 "Targretin Capsules in Combination Therapy May Prolong Survival in Patients with Non-Small Cell Lung Cancer; Data from Phase I-II Trials Published in The Journal of Clinical Oncology," http://www.corporate-ir.net/ireye/ir_site.zhtml?ticker=LGND&script=400 (accessed on Feb. 3, 2005).

Press Release: May 20, 2002, "Clinical Studies of Targretin Capsules and ONTAK Presented at ASCO Underscore Potential of Ligand Drugs to Treat Lung Cancer, Chronic Lymphocytic Leukemia," http://www.corporate-ir.net/ireye/ir_site.zhtml?ticker=LGND&script=400 (accessed on Feb. 3, 2005).

Press Release: May 23, 2000, "Targretin Capsules Shows Activity in Clinical Trials in Patients with Non-Small Cell Lung Cancer and Cutaneous T-Cell Lymphoma," http://www.corporate-ir.net/ireye/ir_site.zhtml?ticker=LGND&script=400 (accessed on Feb. 3, 2005).

Press Release: May 3, 2000, "Targretin(R) Capsules Show Positive Results in Moderate to Severe Plaque Psoriasis; Targretin Capsules Also Effective in Treating All Stages Of CTCL," http://www.corporate-ir.net/ireye/ir_site.zhtml?ticker=LGND&script=400 (accessed on Feb. 3, 2005).

Press Release: Jun. 7, 2004, "Ligand and Investigators Present Exciting Scientific and Clinical Data Updates for Oncology Products Targretin and ONTAK at ASCO Meeting," http://www.corporate-ir.net/ireye/ir_site.zhtml?ticker=LGND&script=400 (accessed on Feb. 3, 2005).

Press Release: Aug. 14, 2000, "Targretin—R—Capsules May Increase Survival in Patients with Non-Small Cell Lung Cancer; Follow-Up Results of Clinical Studies Support FDA Dialogue/ Phase III Program," http://www.corporate-ir.net/ireye/ir_site.zhtml?ticker=LGND&script=400 (accessed on Feb. 3, 2005).

Press Release: Aug. 29, 2000, "Data Suggest Targretin Capsules May Improve Effectiveness of ONTAK Through Upregulation of IL-2 Receptor," http://www.corporate-ir.net/ireye/ir_site.zhtml?ticker=LGND&script=400 (accessed on Feb. 3, 2005).

Press Release: Aug. 29, 2002, "Targretin Increases Susceptibility of Leukemic B- and T-Cells to ONTAK, In Vitro Study of Ligand Products Published in the Journal Blood Demonstrates," http://www.corporate-ir.net/ireye/ir_site.zhtml?ticker=LGND&script=400 (accessed on Feb. 3, 2005).

Ratko et al., "Chemopreventive efficacy of combined retinoid and tamoxifen treatment following surgical excision of a primary mammary cancer in female rats," Cancer Research 49(16): 4472-4476 (1986).

Rendi et al.,"The selective estrogen receptor modulator arzoxifene and the rexinoid LG100268 cooperate to promote transforming growth factor β-dependent apoptosis in breast cancer," Cancer Res. 64(10):3566-71 (2004).

Repa et al., "Regulation of absorption and ABC1-mediated efflux of cholesterol by RXR heterodimers," Science 289(5484):1524-9 (2000).

Rizvi et al., "A Phase I study of LGD1069 in adults with advanced cancer," Clinical Cancer Research 5(7): 1658-1664 (1999).

Rosati et al., "Activity of 9-cis-retinoic acid and receptor-selective retinoids in small cell lung cancer cell lines," Anticancer Res. 18(6A):4071-5 (1998).

Rosenauer et al., "Estrogen receptor expression activates the transcriptional and growth-inhibitory response to retinoids without enhanced retinoic acid receptor alpha expression," Cancer Res. 58(22):5110-6 (1998).

Schulman et al., "Transactivation by retinoid X receptor-peroxisome proliferator-activatedreceptor γ (PPARγ) heterodimers intermolecular synergy requires onlythe PPARγ hormone-dependent activation function," Mol Cell Biol. 18(6):3483-94 (1998).

Shalinsky et al., "Retinoid-induced suppression of squamous cell differentiation in human oralsquamous cell carcinoma xenografts (line 1483) in athymic nude mice," Cancer Res. 55(14): 3183-91 (1995).

Shalinsky et al., "Enhanced antitumor efficacy of cisplatin in combination with ALRT1057 (9-cisretinoic acid) in human oral squamous carcinoma xenografts in nude mice," Clin Cancer Res. 2(3)511-20 (1996).

Shalinsky et al., "A novel retinoic acid receptor-selective retinoid, ALRT1550, has potentantitumor activity against human oral squamous carcinoma xenografts in nudemice," Cancer Res. 57(1)162-8 (1997).

Shao et al., "Three amino acids specify coactivator choice by retinoid X receptors," Mol Endocrinol. 14(8)1198-209 (2000).

Shao et al., "A retinoid-resistant acute promyelocytic leukemia subclone expresses a dominant negative PML-RARα mutation," Blood 89(12): 4282-4289 (1997).

Soignet, et al., "Initial clinical trial of a high-affinity retinoic acid receptor ligand (LGD1550)," Clinical Cancer Research 6(5): 1731-1735 (2000).

Solomin et al., "Retinoid-X receptor signalling in the developing spinal cord," Nature. 395(6700):398-402 (1998).

Song et al., "Abrogation of transforming growth factor-alpha/ epidermal growth factor receptor autocrine signaling by an RXR-selective retinoid (LGD1069, Targretin) in head and neck cancer cell lines," Cancer Research 61(15): 5919-5925 (2001).

Suh et al., "Prevention and treatment of experimental breast cancer with the combination of a new selective estrogen receptor modulator, arzoxifene, and a new rexinoid, LG 100268," Clin Cancer Res. 8(10):3270-5 (2002).

Sun et al., "Differential effects of synthetic nuclear retinoid receptor-selective retinoids on the growth of human non-small cell lung carcinoma cells," Cancer Res. 57(21):4931-9 (1997).

Sun et al., "Identification of receptor-selective retinoids that are potent inhibitors of the growth of human head and neck squamous cell carcinoma cells," Clin Cancer Res. 6(4):1563-73 (2000).

Titcomb et al., "Sensitive and specific detection of retinoid receptor subtype proteins incultured cell and tumor extracts," Mol Endocrinol. 8(7):870-7 (1994).

Vu-Dac et al., "Retinoids Increase Human Apolipoprotein A-II Expression through Activation of the Retinoid X Receptor but Not the Retinoic Acid Receptor," Mol Cell Biol. 16(7):3350-60 (1996).

Wadler et al., "Preliminary phase II clinical and pharmacokinetic study of 9-cis retinoic acid in advanced cervical cancer," Cancer Journal From Scientific American 5(3): 165-170 (1999).

Wagner et al., "Promoter-specific roles for liver X receptor/ corepressor complexes in the regulation of ABCA1 and SREBP1 gene expression," Mol Cell Biol. 23(16):5780-9 (2003).

Wallen-Mackenzie et al., "Nurr1-RXR heterodimers mediate RXR ligand-induced signaling in neuronal cells," Genes Dev. 17(24):3036-47 (2003).

Wu et al., "The retinoid X receptor-selective retinoid, LGD1069, prevents the development of estrogen receptor-negative mammary tumors in transgenic mice," Cancer Res. 62(22):6376-80 (2002).

Wu et al., "Suppression of mammary tumorigenesis in transgenic mice by the RXR- selective retinoid, LGD1069," Cancer Epidemiology Biomarkers & Prevention 11(5): 467-474 (2002).

Wu et al., "9-cis-Retinoic acid suppresses mammary tumorigenesis in C3(1)-simian virus 40 T antigen-transgenic mice," Clinical Cancer Research 6: 3696-3704 (2000).

Yang et al., "Efficient inhibition of activation-induced Fas ligand up-regulation and T cell apoptosis by retinoids requires occupancy of both retinoid X receptors and retinoic acid receptors," J Biol Chem. 270(31):18672-7 (1995).

Zhang et al., "Discovery of novel retinoic acid receptor agonists having potentantiproliferative activity in cervical cancer cells," J Med Chem. 39(14):2659-63 (1996).

Zou et al., "Retinoid X receptor (RXR) ligands activate the human 25-hydroxyvitaminD3-24-hydroxylase promoter via RXR heterodimer binding to two vitaminD-responsive elements and elicit additive effects with 1,25-dihydroxyvitamin D3," J Biol Chem. 272(30):19027-34 (1997).

Zou et al., "Estrogen receptor beta activates the human retinoic acid receptor alpha-1promoter in response to tamoxifen and other estrogen receptor antagonists, but not in response to estrogen," Mol Endocrinol. 13(3):418-30 (1999).

Zugmaier et al., "Growth-inhibitory effects of vitamin D analogues and retinoids on human pancreatic cancer cells," British Journal of Cancer 73(11): 1341-1346 (1996).

Boehm et al. "Retinoids: biological function and use in the treatment of dermatological diseases," Exp. Opin. Invest. Drugs 4(7): 593-612 (1995).

* cited by examiner

METHODS AND PHARMACEUTICAL COMPOSITIONS FOR TREATMENT OF ANTI-ESTROGEN RESISTANT BREAST CANCER USING RXR MODULATORS

RELATED APPLICATION

This application is a continuation of application Ser. No. 09/327,117,. filed Jun. 7, 1999 now abandoned, which claims the benefit of U.S. Provisional Application No. 60/089,104, filed Jun. 12, 1998. The entire disclosures of application Ser. Nos. 09/327,117 and 60/089,104 are hereby incorporated by reference herein.

FIELD OF THE INVENTION

The present invention relates generally to methods and pharmaceutical compositions for treating breast cancer. More particularly, the invention relates to methods and pharmaceutical compositions for treating anti-estrogen resistant breast cancers using retinoid compounds which are RXR modulators.

BACKGROUND OF THE INVENTION

The vitamin A metabolite, retinoic acid, has long been recognized to induce a broad spectrum of biological effects. For example, retinoic acid-containing products, such as Retin-A® and Accutane®, have found utility as therapeutic agents for the treatment of various pathological conditions. In addition, a variety of structural analogues of retinoic acid (i.e., retinoids), have been synthesized that also have been found to be bioactive. Many of these synthetic retinoids have been found to mimic many of the pharmacological actions of retinoic acid, and thus have therapeutic potential for the treatment of numerous disease states.

Medical professionals have become very interested in the therapeutic applications of retinoids. Among their uses approved by the FDA is the treatment of severe forms of acne and psoriasis. A large body of evidence also exists that these compounds can be used to arrest and, to an extent, reverse the effects of skin damage arising from prolonged exposure to the sun. Other evidence exists that these compounds have clear effects on cellular proliferation, differentiation and programmed cell death (apoptosis), and thus, may be useful in the treatment and prevention of a variety of cancerous and pre-cancerous conditions, such as acute promyleocytic leukemia (APL), epithelial cancers, squamous cell carcinomas, including cervical and skin cancers and renal cell carcinoma. Furthermore, retinoids may have beneficial activity in treating and preventing diseases of the eye, cardiovascular disease and other skin disorders. Major insight into the molecular mechanism of retinoic acid signal transduction was gained in 1988, when a member of the steroid/thyroid hormone intracellular receptor superfamily was shown to transduce a retinoic acid signal. Giguere et al., *Nature*, 330:624-29 (1987); Petkovich et al., *Nature*, 330:444-50 (1987); for review, see Evans, *Science*, 240:889-95 (1988). It is now known that retinoids modulate the activity of two distinct intracellular receptor subfamilies; the Retinoic Acid Receptors (RARs) and the Retinoid X Receptors (RXRs), including their subtypes, RARα, β, γ and RXRα, β, γ. Different retinoid compounds exhibit different activities with the retinoid reactor subtypes. For example, all-trans-retinoic acid (ATRA) is an endogenous low-molecular-weight ligand which specifically modulates the transcriptional activity of the RARs, while 9-cis retinoic acid (9-cis) is the endogenous ligand for the RXRs, and activates both the RARs and RXRs. Heyman et al., *Cell*, 68:397-406 (1992); Levin et al., *Nature*, 355:359-61 (1992).

Although both the RARs and RXRs respond to ATRA in vivo due to the in vivo conversion of some of the ATRA to 9-cis, the receptors differ in several important aspects. First, the RARs and RXRs are significantly divergent in primary structure (e.g., the ligand binding domains of RARα and RXRα have only approximately 30% amino acid identity). These structural differences are reflected in the different relative degrees of responsiveness of RARs and RXRs to various vitamin A metabolites and synthetic retinoids. In addition, distinctly different patterns of tissue distribution are seen for RARs and RXRs. For example, RXRα mRNA is expressed at high levels in the visceral tissues, e.g., liver, kidney, lung, muscle and intestine, while RARα mRNA is not. Finally, the RARs and RXRs have different target gene specificity. In this regard, RARs and RXRs regulate transcription by binding to response elements in target genes that generally consist of two direct repeat half-sites of the consensus sequence AGGTCA. RAR:RXR heterodimers activate transcription by binding to direct repeats spaced by five base pairs (a DR5) or by two base pairs (a DR2). However, RXR:RXR homodimers bind to a direct repeat with a spacing of one nucleotide (a DR1). See Mangelsdorf et al., "The Retinoid Receptors" in *The Retinoids: Biology, Chemistry and Medicine*, M. B. Sporn, A. B. Roberts and D. S. Goodman, Eds., Raven Press, New York, N.Y., $2^{nd}$ ed. (1994). For example, response elements have been identified in the cellular retinal binding protein type II (CRBPII), which consists of a DR1, and Apolipoprotein AI genes which confer responsiveness to RXR, but not RAR. Further, RAR has also been recently shown to repress RXR-mediated activation through the CRBPII RXR response element (Mangelsdorf et al., *Cell*, 66:555-61 (1991)). Also, RAR specific target genes have recently been identified, including target genes specific for RARβ (e.g., βRE), which consists of a DR5. These data indicate that the two retinoic acid responsive pathways are not simply redundant, but instead manifest a complex interplay and control distinct biological processes. For example, it has been demonstrated in leukemic cells, activation of RAR pathways regulates cell proliferation and differentiation, whereas activation of RXR pathways leads to the induction of apoptosis.

Retinoid compounds which are RAR and RXR modulators, including both RAR specific and RXR specific modulators, have been previously described. See, e.g., U.S. Pat. Nos. 4,193,931, 4,801,733, 4,831,052, 4,833,240, 4,874,747, 4,877,805, 4,879,284, 4,888,342, 4,889,847, 4,898,864, 4,925,979, 5,004,730, 5,124,473, 5,198,567, 5,391,569, 5,455,265, 5,466,861, 5,552,271, 5,801,253, 5,824,484, 5,837,725 and Re 33,533, and U.S. application Ser. Nos. 08/029,801, 872,707, 944,783, 08/003,223, 08/027,747 and 08/052,050; 60/004,897, 60/007,884, 60/018,318, 60/021,839. See also, WO93/03944, WO93/10094, WO94/20093, WO95/0436, WO97/12853, EP 0718285, Kagechika et al., *J. Med. Chem.*, 32:834 (1989); Kagechika et al., *J. Med. Chem.*, 32:1098 (1989); Kagechika et al., *J. Med. Chem.*, 32:2292 (1989); Boehm et al., *J. Med. Chem.*, 37:2930 (1994); Boehm et al., *J. Med. Chem.*, 38:3146 (1995); Allegretto et al., *J. of Biol. Chem.*, 270:23906 (1995); Bissonnette et al., *Mol. & Cellular Bio.*, 15:5576 (1995); Beard et al., *J. Med. Chem.*, 38:2820 (1995); Dawson et al., *J. Med. Chem.*, 32:1504 (1989).

Breast cancer, like other malignant disease states, is characterized by a loss of cellular growth control followed by invasion of malignant cells into surrounding tissue stroma ultimately leading to metastatic spread of the disease to distant sites within the body. In 1987 over 180,000 new cases of breast cancer were diagnosed in the United States and there were 44,000 deaths due to breast cancer. Breast cancer is currently the second leading cause of cancer deaths in women and the leading cause of cancer deaths in women between the ages of 40 and 55. Population analysis on the incidence of breast cancer demonstrates that one-in-eight women in the United States will develop breast cancer at some point during their life. The primary therapy for breast cancer is surgery, either a partial or modified radical mastectomy with or without radiotherapy. This is typically followed by some form of adjuvant therapy.

The type of adjuvant therapy utilized is often dependant upon the estrogen receptor status of the tumor. Analysis of the hormone status of breast cancers demonstrates that 75% of all breast tumors are estrogen receptor positive and the majority of estrogen receptor positive tumors are found in postmenopausal women.

The anti-estrogen, tamoxifen, is presently the most commonly used drug worldwide for the treatment of breast cancer and approximately 66% of estrogen receptor positive breast cancers will respond to tamoxifen treatment. Tamoxifen is currently the first-line treatment for postmenopausal, estrogen receptor positive women with advanced breast cancer. The mechanism of action of tamoxifen in estrogen receptor positive breast cancer is thought to be due to competitive antagonism at the estrogen receptor of the estrogen driven growth of the tumor. Hence tamoxifen is a cytostatic, not a cytotoxic, agent.

It has previously been shown that as a chemopreventive, the RXR-selective retinoid LGD1069 (Targretin®) is as effective as the anti-estrogen tamoxifen (TAM) at inhibiting mammary carcinoma development in the NMU-treated rat. Gottardis et al., *Can. Res.*, 56:5566-70 (1996).

Clinical evaluation of the efficacy of tamoxifen shows that a significant proportion of patients who initially respond to tamoxifen therapy will acquire resistance, and some on adjuvant tamoxifen therapy will suffer relapses. All advanced breast cancer patients eventually tend to develop tamoxifen resistance. The actual mechanisms underlying the development of tamoxifen resistance are most likely many fold and may involve decreased intra-tumor drug concentration, development of tumor cell clones that are now stimulated to grow in the presence of tamoxifen, and the development of estrogen receptor mutants among others.

Once a tumor develops tamoxifen resistance it will begin to proliferate even in the continued presence of tamoxifen. For breast cancer patients who develop tamoxifen resistance, secondary therapies include second-line hormonal agents such as progestins, aromatase inhibitors and LHRH agonists or cytotoxic chemotherapeutic agents. These commonly utilized second-line agents are at best only effective in approximately 25% of advanced cases. Hence, acquired tamoxifen resistance is the major cause of treatment failure in all stages of breast cancer. Accordingly, a need exists for improved methods and pharmaceutical compositions for treating anti-estrogen or tamoxifen resistant breast cancers.

SUMMARY OF THE INVENTION

The present invention is based on the discovery that RXR modulators can be used to treat breast cancer which is resistant to conventional treatment with anti-estrogen compounds such as tamoxifen. The present invention provides methods for treating such anti-estrogen resistant breast cancers through the administration of retinoid compounds which are modulators of the Retinoid X Receptors (RXRs), including compounds which are selective modulators of RXRs such as LGD1069 (Targetin®), LGD100268, and LGD100324. The present invention also provides pharmaceutical compositions incorporating such RXR modulators that are effective for treating anti-estrogen resistant breast cancer.

These and various other advantages and features of novelty which characterize the invention are pointed out with particularity in the claims annexed hereto and forming a part hereof. However, for a better understanding of the invention, its advantages, and objects obtained by its use, reference should be had to the accompanying figures and descriptive matter, in which there is illustrated and described preferred embodiments of the invention.

BRIEF DESCRIPTION OF THE FIGURES

The present invention may be better understood and its advantages appreciated by those skilled in the art by referring to the accompanying Figures wherein.

DETAILED DESCRIPTION OF THE INVENTION

Figure 1:
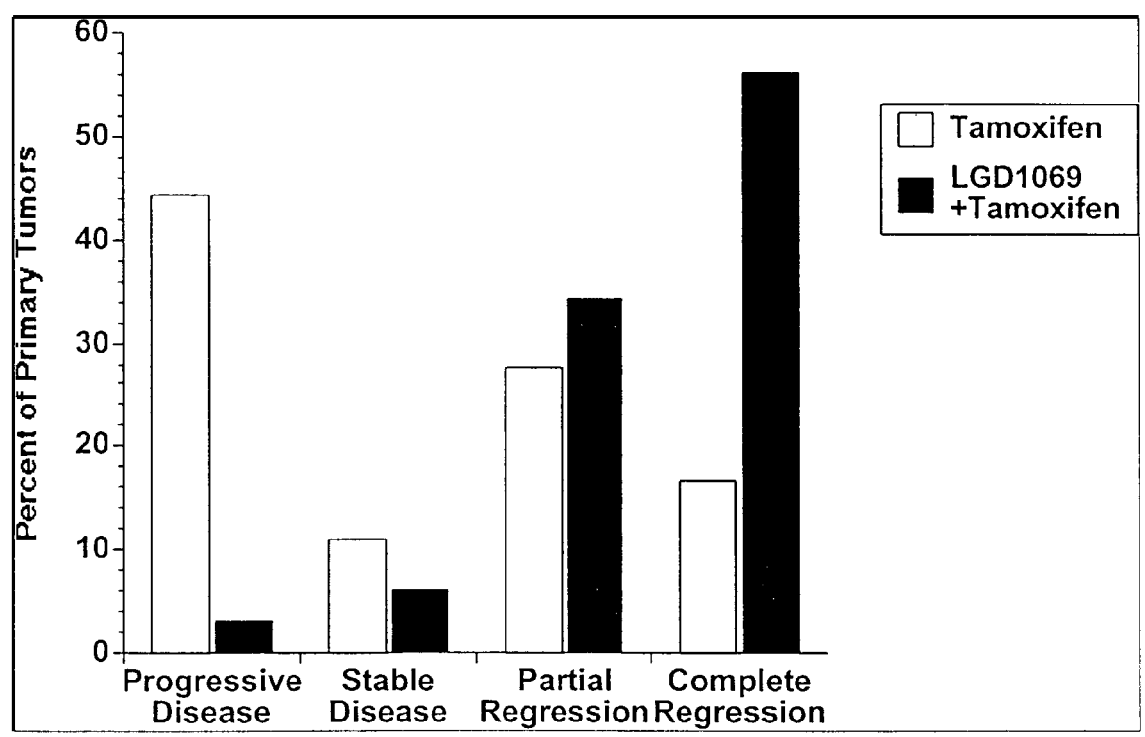
FIG. 1 presents the percentage response of tamoxifen-resistant primary tumors that were continuously treated with tamoxifen and of these tamoxifen-resistant tumors treated with LGD1069/tamoxifen, scored by category.

The present invention relates to methods and pharmaceutical compositions for treating a host having breast cancer which is resistant to conventional treatment with anti-estrogen compounds, such as tamoxifen, by administering to the host a composition containing a pharmaceutically effective amount of an RXR modulator. The host may be a human patient or an animal model of human anti-estrogen resistant breast cancer. The methods and compositions of this invention are adapted to cure, improve or prevent one or more symptoms of anti-estrogen resistant breast cancer in the host. A preferred composition is highly potent and selective with low toxicity.

The term "RXR modulator" refers to a compound or composition which, when combined with a Retinoid X Receptor (RXR), modulates the transcriptional regulation activity of the RXR. RXR modulators include RXR agonists and partial agonists as well as those, which increase the transcriptional regulation activity of RXR homodimers and heterodimers. RXR modulators also include compounds and compositions that preferentially activate RXRs over RARs. Compounds that preferentially activate RXRs over RARs may be referred to as "selective RXR modulators." Compounds and compositions that activate both RXRs and RARs are referred to as "pan agonists", and compounds and compositions that activate RXRs in certain cellular contexts, such as in breast tissue, but not others are referred to as "RXR partial agonists".

Representative RXR modulator compounds which may be used to treat anti-estrogen resistant breast cancer according to the present invention are described in the following U.S. patents and patent applications which are incorporated by reference herein: U.S. Pat. Nos. 5,399,586, 5,466,861, and 5,801,253; U.S. patent application Ser. Nos. 07/809,980, 08/003,223, 08/027,747, 08/045,807, 08/052,050, 08/052, 051, 08/179,750, 08/366,613, 08/480,127, 08/481,877, 08/872,707, and 08/944,783. See, also, WO93/11755, WO 93/21146, WO 94/15902, WO/94/23068, WO 95/04036, and WO 96/20913. Other RXR modulator compounds are also known to those skilled in the art, such as those described for example, in the following articles: Boehm et al. *J. Med. Chem.* 38:3146 (1994), Boehm et al. *J. Med. Chem.* 37:2930 (1994), Antras et al., *J. Biol. Chem.* 266:1157-61 (1991), Salazar-Olivo et al., *Biochem. Biophys. Res. Commun.* 204: 257-263 (1994), and Safanova, *Mol. Cell. Endocrin.* 104: 201 (1994). Such compounds may be prepared according to methods known in the art as described in the aforementioned references, as well as in M. I. Dawson and W. H. Okamura, *Chemistry and Biology of Synthetic Retinoids*, Chapters 3, 8, 14 and 16, CRC Press, Inc., Florida (1990); M. I. Dawson and P. D. Hobbs, *The Retinoids, Biology, Chemistry and Medicine*, M. B. Sporn et al., Eds. (2nd ed.), Raven Press, New York, N.Y., pp. 5-178 (1994); Liu et al., *Tetrahedron*, 40:1931 (1984); *Cancer Res.*, 43:5268 (1983); *Eur. J. Med. Chem.* 15:9 (1980); Allegretto et al., *J. of Biol. Chem.*, 270:23906 (1995); Bissonette et al., *Mol. Cell. Bio.*, 15:5576 (1995); Beard et al., *J. Med. Chem.*, 38:2820 (1995), Koch et al., *J. Med. Chem.*, 39:3229 (1996); and U.S. Pat. Nos. 4,326,055 and 4,578,498.

In a preferred embodiment, RXR modulators which preferentially activate RXRs over RARs, (i.e., selective RXR modulators) are used to treat anti-estrogen resistant breast cancer according to the present invention. For example, RXR selective modulators useful in the present invention include, but are not limited to, the retinoid compounds LGD1069 (Targretin®), LGD100268, and LGD100324, and the congeners, analogs, derivatives and pharmaceutically acceptable salts thereof. The structures of LGD1069, LGD100268, and LGD100324 are shown below, and the synthesis of these compounds is described in U.S. patent application Ser. No. 08/141,496. The synthesis of compounds LGD1069, LGD100268, and LGD100324 is also described in, e.g., WO 94/15902 and Boehm et al., *J. Med. Chem.* 38(16):3146 (1994).

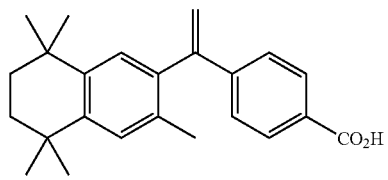

LGD1069
4-[1-(3,5,5,8,8-pentamethyl-5,6,7,8-tetrahydro-2-napthyl)ethenyl]-benzoic acid

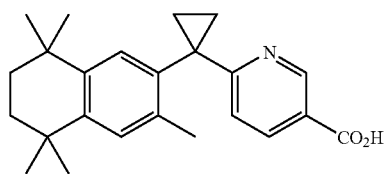

LGD100268
2-[1-(3,5,5,8,8-pentamethyl-5,6,7,8-tetrahydro-2-napthyl)cyclopropyl]-pyridine-5-carboxylic acid

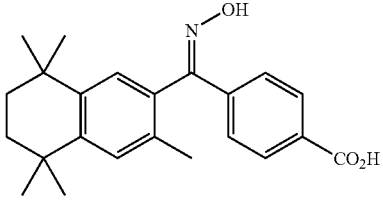

LGD100324
4-[1-(3,5,5,8,8-pentamethyl-5,6,7,8-tetrahydro-2-napthyl)carbonyl]-benzoic acid oxime The ability of a compound or composition to modulate the transcriptional ability of intracellular receptors including RXRs may be measured by assays known to those of skill in the art, including but not limited to the co-transfection (cis-trans) assays. Such assays are described in, e.g., U.S. Pat. Nos. 4,981,784, 5,071,773, 5,298,429, 5,506,102 and U.S. application Ser. Nos. 128,331, 276,536, 426,894, 586, 187, 801,562, 865,878, 07/464,837, 07/882,771, 07/939, 246, 08/045,807, 08/177,740, and 08/179,750 which are incorporated by reference herein. See also, WO89/05355, WO91/06677, WO92/05447, WO93/11235, WO93/23431, WO94/23068, WO95/18380 and CA 2,034,220. For further reference, also see, Heyman et al., *Cell*, 68:397-406 (1992). Such assays may be used to evaluate retinoid compounds to determine activity with the retinoid receptor subtypes RARα, RARβ, RARγ, RXRα, RXRβ, and RXRγ.

Briefly, the co-transfection assay involves the introduction of two plasmids by transient transfection into a retinoid receptor-negative mammalian cell background. The first plasmid contains a retinoid receptor cDNA and directs constitutive expression of the encoded receptor. The second plasmid contains a cDNA that encodes for a readily quantifiable protein, e.g., firefly luciferase or chloramphenicol acetyl transferase (CAT), under control of a promoter containing a retinoid acid response element, which confers retinoid dependence on the transcription of the reporter. In this co-transfection assay, all retinoid receptors respond to all-trans-retinoid acid in a similar fashion. This assay can be used to accurately measure efficacy and potency of retinoic acid and synthetic retinoids as ligands that interact with the individual retinoid receptor subtypes.

For example, the synthetic retinoid compound LGD1069 was evaluated for its ability to regulate gene expression mediated by retinoid receptors. As shown in Table 1, this compound is capable of activating members of the RXR subfamily, i.e., RARα, RARβ, and RARγ, but clearly has no significant activity for members of the RAR subfamily, i.e., RARα, RARβ, and RARγ. Potency and efficacy were calculated for the LGD1069 compound, as summarized in Table 1. Assays of 9-cis-retinoic acid were run for reference, and the results shown in Table 1 demonstrate that these retinoic acid isomers activate members of both the RAR and RXR subfamilies.

TABLE 1

| LDG1069 | Potency (nM) | Efficacy |
|---|---|---|
| RXRα | 40 | 83% |
| RXRβ | 21 | 102% |
| RXRγ | 34 | 80% |
| RARα | >10,000 | 6% |
| RARβ | >10,000 | 17% |

TABLE 1-continued

| LDG1069 | Potency (nM) | Efficacy |
|---|---|---|
| RARγ | >10,000 | 19% |
| 9-cis-retinoic acid | | |
| RXRα | 150 | 140% |
| RXRβ | 100 | 140% |
| RXRγ | 110 | 140% |
| RARα | 160 | 100% |
| RARβ | 5 | 82% |
| RARγ | 47 | 120% |

As shown by the data in Table 1, LGD1069 readily and at low concentrations activates RXRs. Further, LGD1069 is more potent an activator of RXRs than RARs, and preferentially activates RXRs in comparison to RARs, in that much higher concentrations of the compound are required to activate the RARs. In contrast, 9-cis-retionic acid does not preferentially activate the RXRs, as also shown in Table 1. Rather, 9-cis-retinoic acid activates the RARβ and RARγ isoforms at lower concentrations and more readily than the RXRβ and RXRγ isoforms, and has substantially the same, within the accuracy of the measurement, activity for the RARα isoform in comparison to the RXRα isoform.

TABLE 2

| | Potency (nM) | Efficacy |
|---|---|---|
| LDG100268 | | |
| RXRα | 4 | 63% |
| RXRβ | 4 | 93% |
| RXRγ | 3 | 49% |
| RARα | >10,000 | <2% |
| RARβ | >10,000 | <2% |
| RARγ | >10,000 | <2% |
| LDG100324 | | |
| RXRα | 15 | 66% |
| RXRβ | 8 | 51% |
| RXRγ | 12 | 62% |
| RARα | >10,000 | <3% |
| RARβ | >10,000 | <3% |
| RARγ | >10,000 | <3% |

As shown in Table 2 above, LGD100268 and LGD100324 (like LGD1069) readily and preferentially activate RXRs and are more potent an activator of RXRs than of RARs.

In a preferred embodiment, the retinoid compounds and compositions of this invention preferentially activate RXRs in comparison to RARs, are preferably at least three times and more preferably five times more potent as activators of RXRs than RARs, and most preferably ten times more potent as activators of RXRs than RARs, and are more potent as an activator of an RXR than all of RAR isoforms α, β, and γ.

Anti-estrogen resistant breast cancer has been demonstrated to be effectively treated using RXR selective modulators such as, e.g. LGD1069 (Targretin®), as shown in the following examples.

EXAMPLE 1

Mammary tumorigenesis was induced by administration of 50 mg/kg of N-nitroso-N-methylurea (NMU) (Sigma, St. Louis, Mo.) to 50 day old virgin female Sprague-Dawley rats (Harlan-SD, Indianapolis, Ind.). NMU was formulated as an aqueous solution of 10 mg/ml by wetting NMU powder with 3% acetic acid and dissolving it in sterile saline. Fresh solutions of NMU were injected within 30 minutes of preparation. The animals were injected in the tail vein with 5 mg NMU/100 g body weight. Rats were housed in a USDA registered facility in accordance with NIH guidelines for the care and use of laboratory animals. All animals received food (Harlan Teklad LM485-7012, Indianapolis, Ind.) and acidified water ad libitum. Beginning five weeks after tumor induction, animals were examined for tumors twice a week. Tumors were measured with electronic calipers (Mitushoyo, Japan) and cross sectional areas were determined by multiplying the longest length of the tumor by the greatest perpendicular width of the tumor.

When tumors developed (at approximately 6 weeks after initiation) and reached an area of 75 mm$^2$, animals were administered tamoxifen at 800 μg/kg subcutaneously daily for six weeks. After the six week tamoxifen treatment period, animals bearing mammary tumors that did not respond to tamoxifen therapy (tamoxifen resistant) were randomized into two groups. As a control, the first group of animals remained on tamoxifen, while the second group animals remained on tamoxifen and in addition were administered the RXR-agonist LGD1069 (Targretin®) at 100 mg/kg orally daily. Tumor response was monitored for an additional six weeks of therapy, and the following categories were used to score the tumor response: progressive disease—the tumor grew over the course of treatment, and its final area was at least 40% greater than its initial area; stable disease—the tumor did not fluctuate more than 40% from its initial area throughout the course of treatment; partial regression—the tumor regressed more than 40% from its initial area or showed at least two consecutive decreases in area of more than 40% each; and complete regression—the tumor was no longer measurable or no longer palpable.

Figure 2:
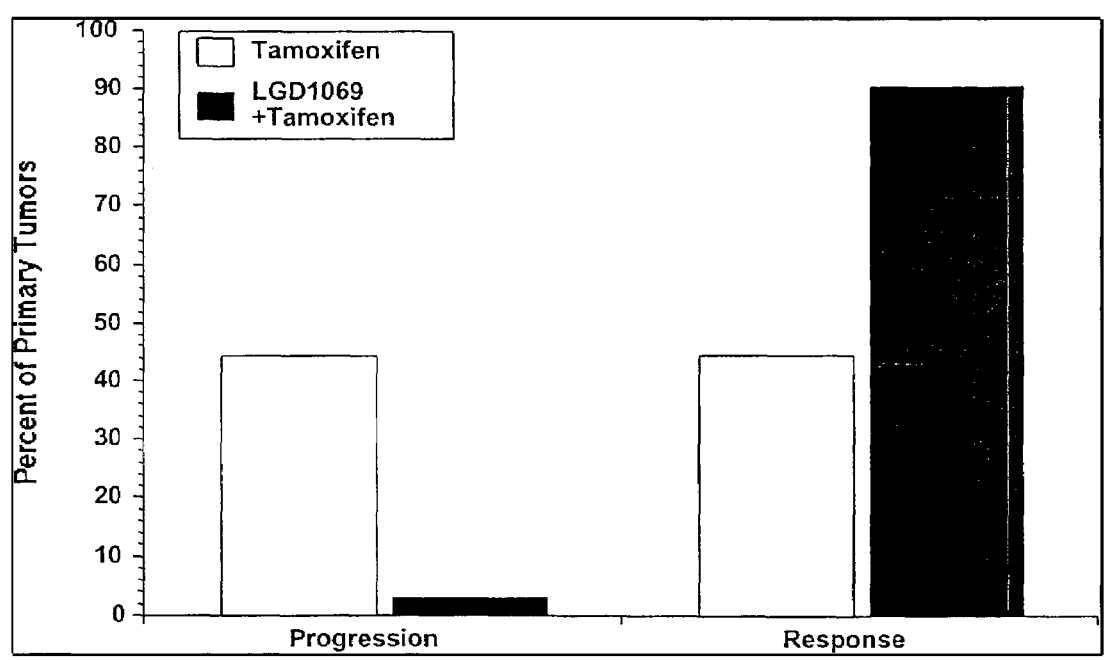
FIG. 2 presents tumor progression and tumor response of the tamoxifen-resistant primary tumors treated with tamoxifen and of these tumors treated with the combination tamoxifen/LGD1069.

FIG. 1 and FIG. 2 show the tumor response of the two groups. These figures show that the addition of LGD1069 to the experimental regimen significantly reduced the incidence of progressive disease from 44% to only 3%, reduced the incidence of stable disease, and increased the incidence of partial and complete regression. As shown in FIG. 1, LGD1069 caused a complete regression of 56% of tumors compared to 16.7% of tumors remaining on tamoxifen alone (p<0.05). As shown in FIGS. 1 and 2, LGD1069 caused a combined response of partial or complete regression in more than 90% of the tumors compared to a 44% response rate in tumors that remained on tamoxifen alone.

EXAMPLE 2

Mammary tumors were induced in Sprague-Dawley rats as in the previous example with NMU and then, beginning one week after carcinogen treatment, animals were treated with low-dose tamoxifen (50 μg/kg, SC) to prevent formation of tumors. Tumors that grew in the presence of the low-dose tamoxifen were evaluated for tamoxifen resistance by increasing the dose of tamoxifen (800 μg/kg, SC), or by adding in LGD1069 (100 mg/kg, PO) to the therapy. The addition of LGD1069 to the therapy significantly reduced the amount of progressive disease in this model, as compared to treatment with tamoxifen.

EXAMPLE 3

Mammary tumors were induced in Sprague-Dawley rats as in Example 1. When tumors developed and reached an area of 75 mm$^2$, animals were randomly assigned to one of three treatment groups and treated daily for six weeks with vehicle, LGD1069 (100 mg/kg), or tamoxifen (800 µg/kg).

After six weeks, in vehicle-treated control animals, 87% of the tumors continued to grow and progress, 8.7% were static, 4.3% partially regressed, and 0% completely regressed. In contrast, in LGD1069-treated animals, 11.1% of tumors continued to progress, 16.7% partially regressed, and 72.2% completely regressed. In tamoxifen-treated animals, 28.6% of tumors continued to progress, 4.8% remained static, 33.3% partially regressed, and 33.3% completely regressed. As shown, treatment with LGD1069 demonstrated significant antitumor efficacy on established mammary tumors and demonstrated greater efficacy than treatment with tamoxifen.

EXAMPLE 4

Mammary tumors were induced in Sprague-Dawley rats as in Example 1. Animals treated with LGD1069 at the submaximally efficacious dose of 10 mg/kg showed that 10.5% of primary mammary tumors regressed. Animals treated with tamoxifen at the submaximally efficacious dose of 150 mg/kg showed that 5.6% of primary mammary tumors regressed. However, when the two compounds where coadministered, a significantly greater effect was achieved, with 26.3% of the tumors completely regressing.

As shown by the above examples, the administration of RXR modulators such as LGD1069 has now been shown to demonstrate anti-tumor efficacy on mammary tumors that are tamoxifen resistant and that fail tamoxifen therapy. Accordingly, the use of RXR modulators such as, e.g., LGD1069, has been demonstrated to be useful as both an adjuvant treatment for breast cancer as well as a treatment for patients who have failed tamoxifen therapy.

Hormonal receptor status is a factor in determining whether a tumor is anti-estrogen resistant. Tamoxifen, an anti-estrogen, is primarily effective in tumors that have estrogen receptor (ER) positive status. Tumors that have estrogen receptor negative (ER) status are generally unresponsive to tamoxifen. The hormonal status of a breast cancer may be determined by staining the tumor cells for ER receptors, or by other conventional techniques for detecting the presence of ER receptors. During disease progression, the tumor cell DNA becomes increasingly mutated. Highly mutated DNA often exhibits an advanced rate of tumor cell growth. Abnormal tumor cell DNA and a fast rate of tumor growth are often present in anti-estrogen resistant cells indicating that tamoxifen therapy may be ineffective.

Since RXR selective modulators have been shown as effective in adjuvant treatment of tamoxifen resistant breast tumors, treatment with RXR selective modulators is therefore useful for treatment of ER negative breast tumors. This includes those patients who have either failed tamoxifen therapy or have ER negative status tumors for which tamoxifen therapy would not be considered.

According to the invention, a host having anti-estrogen resistant breast cancer is treated with a pharmaceutically effective amount of an RXR modulator. By pharmaceutically effective amount is meant an amount of a pharmaceutical compound or composition having a therapeutically relevant effect on anti-estrogen resistant breast cancer. A therapeutically relevant effect relieves to some extent one or more symptoms of anti-estrogen resistant breast cancer in a patient or returns to normal either partially or completely one or more physiological or biochemical parameters associated with or causative of anti-estrogen resistant breast cancer.

In another aspect, this invention features a pharmaceutical composition specially formulated for treating anti-estrogen resistant breast cancer containing a pharmaceutically effective amount of a RXR modulator and a pharmaceutically acceptable carrier adapted for a host, particularly a human, having anti-estrogen resistant breast cancer. A composition containing a pharmaceutically effective amount of an RXR modulator may be administered orally or systemically to a host. In a preferred embodiment, it is administered orally.

In a preferred embodiment, the composition is held within a container that includes a label stating to the effect that the composition is approved by the FDA in the United States (or an equivalent regulatory agency in a foreign country) for treating anti-estrogen resistant breast cancer. Such a container provides a therapeutically effective amount of the active ingredient to be administered to a host.

In pharmaceutical compositions of the present invention, the RXR modulator is mixed with suitable carriers or excipient(s). In treating a patient exhibiting anti-estrogen resistant breast cancer, a therapeutically effective amount of an agent or agents such as these is administered. A therapeutically effective dose refers to that amount of the compound that results in amelioration of symptoms or a prolongation of survival in a patient.

The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. See, e.g., U.S. Pat. Nos. 5,409,930, 5,656,643, and 5,710,158. See also, WO 92/20642 and WO 95/15758). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. Evaporating the solution then isolates the salt. In another example, the salt is prepared by a reaction of the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents.

Toxicity and therapeutic efficacy of such compounds can be determined by standard pharmaceutical procedures in cell cultures or experimental animals, for example, for determining the $LD^{50}$ (the dose lethal to 50% of the population) and the $ED^{50}$ (the dose therapeutically effective in 50% of the population). The dose ratio between toxic and therapeutic effects, the therapeutic index, can be expressed as the ratio $LD^{50}/ED^{50}$. Compounds that exhibit large therapeutic indices are preferred. The data obtained from these cell culture assays and animal studies can be used in formulating a range of dosages for use in humans. The dosage of such compounds lies preferably within a range of circulating concentrations that include the $ED^{50}$ with little or no toxicity. The dosage may vary within this range depending upon the dosage form employed and the route of administration utilized. Levels in plasma may be measured, for example, by HPLC.

The individual physician in view of the patient's condition can choose a route of administration, dosage, and exact formulation. (e.g., Fingl et al., *The Pharmacological Basis of Therapeutics* Ch. 1, (1975)). It should be noted that the attending physician would know how to and when to terminate, interrupt, or adjust administration due to toxicity, or to organ dysfunction. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the disclosure provided herein. In addition to the active ingredients, these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions. The pharmaceutical compositions of the present invention may be manufactured in a manner that is itself known, for example, by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dye stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Liposomes may be used for encapsulated delivery.

Pharmaceutical formulations disclosed or described in Boehm et al., U.S. application Ser. Nos. 08/003,223; 08/027,747; 08/052,051, incorporated by reference herein. See also, WO94/15902 for further reference.

All publications referenced are incorporated by reference herein, including the nucleic acid sequences and amino acid sequences listed in each publication. All the compounds disclosed and referred to in the publications mentioned above are incorporated by reference herein, including those compounds disclosed and referred to in articles cited by the publications mentioned above.

We claim:

1. A method for treating a host having anti-estrogen resistant breast cancer, comprising administering to said host tamoxifen and a selective Retinoid X Receptor (RXR) modulator, wherein the tamoxifen and the selective RXR modulator are administered in amounts that together are pharmaceutically effective, and thereby treating a host having anti-estrogen resistant breast cancer.

2. The method of claim 1, wherein said selective RXR modulator is selected from the group consisting of LGD1069, LGD100268 and LGD100324.

3. The method of claim 1, wherein said selective RXR modulator selectively activates one or more RXRs in preference to each of RAR isoforms α, β and γ.

4. The method of claim 1, wherein the tamoxifen and the selective RXR modulator are administered at the same time.

5. The method of claim 1, wherein the host having anti-estrogen resistant breast cancer has previously been treated with an anti-estrogen compound.

6. The method of claim 1, wherein the host having anti-estrogen resistant breast cancer has previously been treated with tamoxifen.

7. The method of claim 1, wherein the anti-estrogen resistant breast cancer is capable of growing in the presence of at least one anti-estrogen compound.

8. A method for treating a host having tamoxifen resistant breast cancer, comprising administering to said host tamoxifen and a selective RXR modulator, wherein the tamoxifen and the selective RXR modulator are administered in amounts that together are pharmaceutically effective.

9. The method of claim 8, wherein said selective RXR modulator is selected from the group consisting of LGD1069, LGD100268, and LGD100324.

10. The method of claim 8, wherein said selective RXR modulator selectively activates one or more RXRs in preference to each of RAR isoforms α, β, and γ.

11. The method of claim 8, wherein the tamoxifen and the selective RXR modulator are administered at the same time.

12. The method of claim 8, wherein the host having tamoxifen resistant breast cancer has previously been treated with an anti-estrogen compound.

13. The method of claim 8, wherein the host having tamoxifen resistant breast cancer has previously been treated with tamoxifen.

14. The method of claim 8, wherein the tamoxifen resistant breast cancer is capable of growing in the presence of at least one anti-estrogen compound.

15. A method for treating a host having anti-estrogen resistant breast cancer, comprising administering to said host a pharmaceutically effective amount of a composition comprising tamoxifen and a selective RXR modulator.

16. A method for treating a host having tamoxifen resistant breast cancer, comprising administering to said host a pharmaceutically effective amount of a composition comprising tamoxifen and a selective RXR modulator.

17. A method for improving the efficacy of treating a host having anti-estrogen resistant breast cancer with tamoxifen, comprising administering to said host a pharmaceutically effective amount of a selective RXR modulator.

18. A method for improving the efficacy of treating a host having tamoxifen resistant breast cancer with tamoxifen, comprising administering to said host a pharmaceutically effective amount of a selective RXR modulator.

* * * * *

UNITED STATES PATENT AND TRADEMARK OFFICE
CERTIFICATE OF CORRECTION

| | | |
|---|---|---|
| PATENT NO. | : 7,259,188 B2 | |
| APPLICATION NO. | : 10/229649 | |
| DATED | : August 21, 2007 | |
| INVENTOR(S) | : Lamph et al. | |

It is certified that error appears in the above-identified patent and that said Letters Patent is hereby corrected as shown below:

IN THE TITLE PAGES:
In Item [73] Assignee:
  please replace "Llgand" with --Ligand--

On The Title Page,
In Item [56] References Cited, in OTHER PUBLICATIONS:
   in Beard, et al., please replace "Heteromatic" with --Heteroaromatic--
   in the first Boehm, M. et al., please replace "(994)" with --(1994)--
   in the third Allegretto et al., please replace "if" with --of--
   in Blumberg et al., please insert --Acad.-- between "Natl." and "Sci."
   in the third Boehm et al., please replace "itsapplication" with --its application--
   in Canan Koch et al., please replace "ofadipogenesis" with --of adipogenesis--
   in Elgort et al., please replace "thehuman" with --the human--
   in Hamman, L.G., please replace "Xreceptor" with --X receptor--
   in Howell et al., please replace "receptorselectivity" with --receptor selectivity--
   in Lee et al., please replace "requiresretinoid" with --requires retinoid--
   in Mukherjee et al., please replace "peroxisomeproliferator-activated" with
       --peroxisome proliferator-activated--, and please replace "andactivation" with
       --and activation--
   in the first Schulman et al., please replace "proliferator-activatedreceptor" with
       --proliferator-activated receptor--, and please replace "onlythe" with --only the--
   in the first Shalinsky et al., please replace "oralsquamous" with --oral squamous--
   in the third Shalinsky et al., please replace "nudemice" with --nude mice--

UNITED STATES PATENT AND TRADEMARK OFFICE
CERTIFICATE OF CORRECTION

PATENT NO. : 7,259,188 B2
APPLICATION NO. : 10/229649
DATED : August 21, 2007
INVENTOR(S) : Lamph et al.

It is certified that error appears in the above-identified patent and that said Letters Patent is hereby corrected as shown below:

On the Title Page Item [56]
  in Zhang et al., please replace "potentantiproliferative" with --potent antiproliferative--

At column 1, line 9, please replace "09/327,117,." with --09/327,117,--

Signed and Sealed this

First Day of January, 2008

JON W. DUDAS
*Director of the United States Patent and Trademark Office*